US009301928B2

(12) United States Patent  (10) Patent No.: US 9,301,928 B2
Asmus et al.  (45) Date of Patent: *Apr. 5, 2016

(54) CONFORMABLE COATING AND COMPOSITION

(71) Applicant: 3M INNOVATIVE PROPERTIES COMPANY, Saint Paul, MN (US)

(72) Inventors: Robert A. Asmus, Hudson, WI (US); Hae-Seung Lee, Woodbury, MN (US); John D. Dell, Saint Paul, MN (US); Deena M. Conrad-Vlasak, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/346,481

(22) PCT Filed: Sep. 28, 2012

(86) PCT No.: PCT/US2012/057855
§ 371 (c)(1),
(2) Date: Mar. 21, 2014

(87) PCT Pub. No.: WO2013/049527
PCT Pub. Date: Apr. 4, 2013

(65) Prior Publication Data
US 2014/0228475 A1   Aug. 14, 2014

Related U.S. Application Data

(60) Provisional application No. 61/541,426, filed on Sep. 30, 2011, provisional application No. 61/673,587, filed on Jul. 19, 2012.

(51) Int. Cl.
| *A61K 6/08* | (2006.01) |
| *A61L 24/06* | (2006.01) |
| *A61K 9/70* | (2006.01) |
| *C09D 109/06* | (2006.01) |
| *A61L 26/00* | (2006.01) |
| *A61L 24/04* | (2006.01) |
| *A61K 31/275* | (2006.01) |
| *C09D 153/02* | (2006.01) |

(52) U.S. Cl.
CPC .............. *A61K 9/7007* (2013.01); *A61K 31/275* (2013.01); *A61L 24/043* (2013.01); *A61L 24/06* (2013.01); *A61L 26/0014* (2013.01); *C09D 109/06* (2013.01); *C09D 153/02* (2013.01)

(58) Field of Classification Search
CPC ........ A61L 24/043; A61L 24/06; C08L 35/00
USPC ................................................. 523/111, 118
See application file for complete search history.

(56) References Cited

U.S. PATENT DOCUMENTS

| 3,264,249 | A | * | 8/1966 | Araki et al. ................... 523/118 |
| 3,940,362 | A | | 2/1976 | Overhults |
| 4,230,815 | A | | 10/1980 | Itoh |
| 4,987,893 | A | | 1/1991 | Salamone |
| 5,103,812 | A | | 4/1992 | Salamone |
| 5,140,084 | A | | 8/1992 | Mikuni |
| 5,259,835 | A | | 11/1993 | Clark |
| 5,328,687 | A | | 7/1994 | Leung |
| 5,369,130 | A | | 11/1994 | Numata |
| 5,928,611 | A | | 7/1999 | Leung |
| 5,981,621 | A | | 11/1999 | Clark |
| 6,010,714 | A | | 1/2000 | Leung |
| 6,103,814 | A | | 8/2000 | vanDrongelen |
| 6,143,352 | A | | 11/2000 | Clark |
| 6,143,805 | A | | 11/2000 | Hickey |
| 6,183,593 | B1 | | 2/2001 | Narang |
| 6,217,603 | B1 | | 4/2001 | Clark |
| 6,488,944 | B2 | | 12/2002 | Narang |
| 6,565,840 | B1 | | 5/2003 | Clark |
| 6,607,631 | B1 | | 8/2003 | Badejo |
| 7,001,947 | B2 | | 2/2006 | Cordova |
| 7,479,530 | B2 | | 1/2009 | Hughes |
| 7,641,893 | B2 | | 1/2010 | Salamone |
| 2006/0173124 | A1 | | 8/2006 | Paul et al. |
| 2007/0041935 | A1 | | 2/2007 | Salamone |

FOREIGN PATENT DOCUMENTS

| CN | 1273089 | 11/2000 |
| CN | 1733317 | 2/2006 |
| EP | 0026665 | 4/1981 |
| WO | WO 2013-049543 | 4/2013 |

OTHER PUBLICATIONS

Sugihara, "The Extensibility in Human Skin: variation according to age and site", British Journal of Plastic Surgery, 1991, vol. 44, pp. 418-422.

International Search Report for PCT International Application No. PCT/US2012/057855 Mailed on Dec. 4, 2012, 3 pages.

* cited by examiner

*Primary Examiner* — Tae H Yoon
(74) *Attorney, Agent, or Firm* — 3M Innovative Properties Company; Lynn R. Hunsberger

(57) ABSTRACT

The disclosed conformable coating provides a highly durable and resilient film useful for protecting and repairing surfaces such as skin and mucous membranes. The coating comprises 0.1% to 65% wt. of a polymerized cyanoacrylate monomer and at least 35% wt. of an elastomer phase. The conformable coating composition comprises a polymerizable cyanoacrylate monomer, an elastomer, and a volatile liquid. The cyanoacrylate monomer is 0.1 to 65% wt. of the nonvolatile portion, the elastomer in an elastomer phase is at least 35% wt. of the nonvolatile portion, and the volatile liquid is at least 40% wt. of the total composition.

14 Claims, No Drawings though protection of skin is of primary interest. The coating can be very useful in patients subject to barrier breakdown such as incontinent patients, ostomy patients, patients undergoing radiation therapy, patients with peristomal skin conditions, and others. The coating as a liquid or film can also be used to adhere medical devices to the skin, such as ostomy pouching systems, wound dressings, catheter fixation devices, and other medical devices that are adhered directly to the skin.

CONFORMABLE COATING AND COMPOSITION

CROSS REFERENCE TO RELATED APPLICATIONS

This application is a national stage filing under 35 U.S.C. 371 of PCT/US2012/057855, filed Sep. 28, 2012, which claims priority to U.S. Provisional Application No. 61/541,426, filed Sep. 30, 2011, and to U.S. Provisional Application No. 61/673,587, filed Jul. 19, 2012, the disclosures of which are incorporated by reference in their entirety herein.

FIELD

The present disclosure relates to a conformable coating composition that comprises a polymerizable cyanoacrylate monomer, an elastomer, and a volatile liquid. The present disclosure relates to a conformable coating comprising a polymerized cyanoacrylate monomer and an elastomer.

BACKGROUND

Barrier products are used to protect the skin of patients who have incontinence, skin occlusion, frequent washes, ostomys, especially ileostomy and colostomies. The presence of high moisture and corrosive enzymes from body fluids can lead to devastating breakdown of the skin, which can then lead to fungal infection, denuding, and erosion of the skin.

Commonly used products for protecting skin are occlusive barrier pastes. These barrier pastes are messy to apply and clean up. Also, the pastes interfere with the securement of ostomy devices.

Liquid, film-forming products have also been developed to be applied and to protect skin, such as disclosed in U.S. Pat. Nos. 5,103,812 and 4,987,893. To increase the durability liquid, film forming products, cyanoacrylates have been used such as disclosed in U.S. Pat. Nos. 6,183,593 and 6,143,805. Cyanoacrylates very quickly form a film over skin, and even over moist skin. Therefore, there is a risk of adhering two skin surfaces together. U.S. Pat. No. 7,641,893 discloses cyanoacrylates used in a conformable bandage and coating material for application to skin, and includes volatile liquid to limit two of the cyanoacylate-containing surface from sticking together. However, even with these advances in cyanoacylate-containing compositions for application to skin, cyanoacrylate containing coating are brittle and do not flex well on skin.

SUMMARY

The disclosed conformable coating provides a highly durable and resilient film useful for protecting and repairing surfaces such as skin and mucous membranes. The conformable coating composition comprises a polymerizable cyanoacrylate monomer, an elastomer, and a volatile liquid. A coating formed from the conformable coating composition comprises a polymerized cyanoacrylate and an elastomer.

In one embodiment of the conformable coating composition the cyanoacrylate monomer is 0.1 to 65% wt. of the nonvolatile portion, the elastomer in an elastomer phase is at least 35% wt. of the nonvolatile portion, and the volatile liquid is at least 40% wt. of the total composition. In one embodiment, the polymerizable cyanoacrylate monomer component comprises alpha-cyanoacrylates. In one embodiment, the alpha-cyanoacrylate monomer component comprises at least one of: n-butyl cyanoacrylate and 2-octyl cyanoacrylate. In one embodiment, the composition comprises 0.1 to 55% wt. of the nonvolatile portion of the polymerizable cyanoacrylate monomer. In one embodiment, the volatile liquid is selected from the group consisting of volatile linear and cyclic siloxanes, volatile polydimethylsiloxanes, isooctane, octane, cyclohexane, a solvent blend of isooctane and ethyl acetate, and combinations thereof. In one embodiment, the composition comprises at least 60% wt. of the total composition of the volatile liquid. In one embodiment, the elastomer is a rubber or a thermoplastic elastomer. In one embodiment, the rubber is selected from the group consisting polyisobutylenes, polyisoprenes, polybutadiene, butyl rubber, halogenated butyl rubbers, dienes, styrene rubber copolymers, acrylonitriles, and copolymers or mixtures thereof, which are soluble or highly swollen in the volatile liquid.

In one embodiment, the elastomer is a rubber modified with a low surface energy material. In one embodiment, the elastomer is siliconized rubber. In one embodiment, the siliconized rubber is saturated. In one embodiment, the siliconized rubber is unsaturated. In one embodiment, the composition comprises 50% to 99% wt. of the nonvolatile portion of the elastomer. In one embodiment, the composition does not create an adhesive bond which exceeds 45 grams shear force over a 6.5 cm$^2$ area after 10 min. contact time to a second glass surface, when: (i) the composition is applied to a first glass surface, and (ii) the second glass surface is applied to the first glass surface, having the composition disposed there between, wherein the composition forms an adherent, conformable polymer coating when applied to a surface. In one embodiment, the composition further comprises a silane-containing polymer. In one embodiment, the composition further comprises an anti-blocking agent.

In one embodiment, a conformable film comprises 0.1% to 65% wt. of a polymerized cyanoacrylate monomer and at least 35% wt. of an elastomer phase of the elastomer. In one embodiment, the conformable film has a thickness of less than 1 mm. In one embodiment, the conformable film fractures less than 75% at 100% elongation. In one embodiment, the conformable film fractures less than 75% at 200% elongation. In one embodiment the conformable film has an elongation of at least 50%. In one embodiment, the elastomer is a siliconized rubber. In one embodiment, the siliconized rubber is an unsaturated rubber. In one embodiment, the polymerized cyanoacrylate and elastomer copolymerize.

DETAILED DESCRIPTION

The cyanoacrylate monomers and volatile, non-reactive liquids when containing a elastomer and when polymerized provide for a fast drying, hemostatic, adherent, non-stinging and non-irritating liquid adhesive coating that inhibits adhesion of two surfaces to each other and that is resilient and flexible. Although polymerized cyanoacrylate coatings are typically brittle, inclusion of an elastomer into the composition greatly increases the stretch and recovery ability of the coating without introducing crack or breaks in the coating. Additionally, although inclusion of an elastomer into the composition can increase the surface tack of the coating, it was surprisingly found that the coatings could be designed to have a relatively low coefficient of friction, or drag.

The coating compositions, comprised of the cyanoacrylate monomer, volatile solvent, and elastomer when formed as a coating are useful for protecting or treating skin, nails, tissues, organs and mucous membranes, e.g. bleeding injuries, surgical sites, skin ulcers, cuts, abrasions, incisions, cold sores, blisters, rashes, abraded gums and other oral surfaces, hemorrhoids and abraded body areas, and other mucosal membrane incisions and wounds. The coatings may also be used as surgical glues. A coating formed from the conformable coating composition comprises a solvent borne or dispersion of an elastomer and cyanoacrylate.

Depending on the particular requirements of the user, the compositions can be applied by known means, such as with a spray, pump, swab, rod, sterile brush or medicine dropper that may be single use or multi use items.

Cyanoacrylate monomers that may be used include readily polymerizable alpha-cyanoacrylates, including alkyl cyanoacrylates, aryl cyanoacrylates, alkoxyalkyl cyanoacrylates, such as butyl cyanoacrylate and n-butyl cyanoactylate in particular, octyl cyanoacrylate and 2-octyl cyanoacrylate in particular, ethyl cyanoacrylate, methyl cyanoacrylate, n-dodecyl cyanoacrylate, phenyl 2-cyanoacrylate, methoxyethyl 2-cyanoacrylate, and the like. The composition may be composed of one or more polymerizable cyanoacrylate monomers. In one embodiment, the cyanoacrylate monomer is present from about 0.1% to about 99.9%, in another embodiment 0.1% to about 65%, in another embodiment, 0.1% to about 55%, by weight of the nonvolatile portion of the conformable coating composition. In one embodiment, the cyanoacrylate is present in at least 5%, by weight, of the nonvolatile portion of the composition, so that the system demonstrates good hemostatic and lymphostatic performance.

The elastomers that may be used in the conformable coating composition include natural or synthetic rubber and thermoplastic elastomers. Suitable rubbers include, but are not limited to, low to high molecular weight versions of the following: polyisobutylenes, polyisoprenes, butyl rubber, halogenated butyl rubbers, dienes, styrene copolymers, acrylonitrile copolymers, and copolymers or mixtures thereof, which are soluble or highly swollen in the volatile liquid and cyanoacrylate system. In one embodiment, the molecular weight of the elastomer or overall elastomer system (if a blend of elastomers) is from 1400 to 1,000,000. In one embodiment, the molecular weight of the primary elastomer is from 1,400 to 1,000,000, in one embodiment 10,000 to 1,000,000, in one embodiment 25,000 to 600,000, and in one embodiment 50,000 to 200,000. In one embodiment a lower molecular weight (1 to 60,000) elastomer may be blended into the elastomer system. The "elastomer phase" is defined to be the total formula solids of the coating minus the weight % of the cyanoacrylate phase.

Although prior systems have included rubber components, these prior systems included low concentrations of rubber to toughen the formed film that do not constitute the continuous phase. The disclosed conformable coating composition comprises at least 35% wt. of an elastomer phase of the nonvolatile portion of the conformable coating composition. In one embodiment, the conformable coating composition comprises at least 50% wt. of an elastomer phase of the nonvolatile portion of the conformable coating composition. The addition of high concentrations of elastomers, and rubber elastomers in particular, have been found to enable the conformable coating to survive high elongation and have excellent adhesion and durability to the substrate, typically skin. In one embodiment, the ratio of cyanoacrylate, in one embodiment butyl cyanoacrylate, to elastomer phase, in one embodiment rubber, is in the range of 10:90 to 40:60 to ensure the system is elastomeric.

Inclusion of elastomers in the conformable coating composition can demonstrate blocking behavior. The coating on the surface will not feel tacky but when two of the coated surfaces come in contact with one another, the coated surfaces show an affinity to each other and will adhere. Further, the elastomer components can also increase the frictional forces, or drag, between the conformable coating and an external surface, such as bedding or clothing. In one embodiment, the composition further comprises an anti-blocking agent. An anti-blocking agent may be a waxy material, such as cetyl palmitate or polyvinyl stearyl ether, or it may be an aromatic high Tg resin such as polystyrene or a C9 aromatic resin of a methylated derivative of styrene, or copolymers that may be included in the conformable coating composition. Surprisingly, these materials provided clear cured films which have superior wear performance Other waxy materials such as fatty alcohol, fatty alcohol esters and ethers as well as waxy polymers could also be used to reduce blocking.

In another embodiment, chemically modifying the elastomer with a low surface energy component has been found to reduce the blocking behavior and reduce the drag forces. Simply including anti-blocking agents into the composition did reduce the final tack of the film. However, the anti-blocking agents negatively impacted the overall elongation properties of the film. The chemically modified elastomer showed both a reduction in tack of the film, reduction in blocking behavior, reduction in drag, while still providing the elongation properties to the film.

Specifically, silicone, fluorinated oligomers, and hydrocarbon based oligomeric material can be used to modify the elastomer. The modification can be accomplished by grafting or hydrosilylation. In one embodiment, dimethicone is used to modify the rubber and specifically is used to modify an unsaturated rubber.

The molecular weight of the low surface energy portion impacts the ability of the low surface energy portion to have an effect on drag. For example, a very low molecular weight of a dimethicone had little effect on reducing drag. Too high of a molecular weight of the low surface energy side chain can cause solubility issues within the system. It is believed that either the modified elastomer is poorly soluble in the solvent or the modified elastomer is not miscible with other elastomers in solution. In one embodiment, the side-chain of the low surface energy portion is between 500 and 10,000 molecular weight.

The elastomer can have one or more side-chains of the low surface energy portion. Too many side-chains of the low surface energy portion can negatively impact the barrier performance of the resulting film. In one embodiment, if the elastomer is a saturated rubber, the amount of dimethicone should not exceed much above 60%. In one embodiment, unsaturated rubbers are able to withstand much higher levels of side chain modification, specifically with dimethicone, approaching 99% since the abundant unsaturation may ultimately be used for the grafting reaction and/or may ultimately be copolymerized into the other components of the composition.

In one embodiment, a rubber is the elastomer to which a low surface energy component is included. The saturated or unsaturated rubbers may be modified. However, unsaturated rubbers perform particularly well. Without being limited to any one theory, it is believe that the unsaturated, modified rubbers are capable of copolymerizing with the cyanoacrylates during curing to produce an interpenetrating network which is nontacky and more resistant to blocking. Example of saturated rubbers are styrene-ethylene/butylene-styrene copolymer, styrene ethylene propylene styrene block copolymer, polyisobutylene, ethylene-propylene, ethylene-butene, and ethylene-octene. Examples of unsaturated rubbers are polydienes, polyisoprene, natural rubber, styrene-butadiene, styrene-isoprene, butyl rubber, acrylonitrile-butadiene, halogenated rubber such as polychloroprene, EPDM rubber, and polybutadiene as well as copolymers of these rubber with polyisobutylene.

Selection of the elastomer is guided by several properties which are sometimes antagonistic to one another. The properties are adhesion to skin, elongation, barrier properties, hardness, toughness, tackiness, draggy feel and blocking Generally softer and lower molecular weight elastomers, and rubbers in particular, or blends of higher molecular weight with lower molecular elastomers (1-60,000 molecular weight) provide optimal adhesion to skin. However, these materials tend to all have the highest blocking, highest drag and softest feel on skin. In order to reduce the surface drag and blocking, increasing the hardness of the elastomer offsets these problems. There are several approaches to increasing the hardness, if the elastomer contains a crystallizing polymer increasing its volume fraction will help increase hardness. In the case of polystyrene copolymers, increasing the styrene phase as a percentage of end block segment or adding the styrene phase to the midblock is also effective for increasing hardness. Addition of high Tg modifying resins is also effective at increasing hardness. Reasonable levels of the modifying resins range from 1 to 150% wt. of the elastomer content of the coating. More preferred, the range of modifying resin is 20 to 100% wt. of the elastomer content. In one embodiment, these increases in hardness do not come at a loss of elongation and adhesion to skin. The effectiveness of these modifiers can be assessed using the Elongation test method disclosed at 100 and 200% elongation. It is desired that the tested films will have less than 75% failure, preferably less than 50% failure, more preferably less than 25% failure, and of course ideally no failure.

We have unexpectedly found increasing the styrene content of SEBS rubbers from 12% to 18% dramatically improves blocking resistance. We have unexpectedly found increasing the styrene content of SEBS rubbers from 12% to 18% dramatically improves blocking resistance. In one embodiment, the range of the styrene content of the styrene copolymer elastomer is from 0.1% to 65% wt., in one embodiment from 10% to 55% wt., and in one embodiment 18 to 45% wt. Increasing the styrene content of these copolymers reduces the solubility of the systems in alkane solvents such as isooctane, however cyclic solvents like cyclohexane enable solubility of very high styrene contents exceeding 40%.

The molecular weight of the polymer as well as its crystallinity and copolymer content influences the viscosity of the composition. Ideally the viscosity of the composition is less than 1,000 cps, and preferably below 100 cps. Targeting a low viscosity and yet maintaining as high a coating solids as possible is desired for delivering an adequate film thickness on skin by a foam pad or swab applicator. Preferred thermoplastic elastomers are at the lower range of the available molecular weight range. Selection of preferred candidates is made by solvating the elastomer in the desired solvent and determining the maximum concentration before the viscosity exceeds the desired target. In one embodiment, the coating composition has viscosity of 1,000 cps and less at solids levels above 10%.

It is desired that the amount of solution applied to the substrate, such as skin, be in the range of 10 to 100 mg/square inch. Based on solids contents ranging from 10 to 30% the likely coating weight of the dried film will range from 1 to 30 mg/square inch.

The cyanoacrylate monomers and elastomer are incorporated into a solvent system comprising non-stinging, non-irritating, volatile, non-reactive liquids. The non-stinging, non-irritating solvent system can comprise volatile liquid siloxanes, such as hexamethyldisiloxane (HMDS), octamethylcyclotetrasiloxane, decamethylcyclopentasiloxane, octamethyltrisiloxanes and the like. Other volatile solvents, including volatile organosilicones, such as caprylyl methicone, ethyl trisiloxane, and the like; (C6 to C10) alkanes, such as isooctane, octane, nonane and decane (and their structural isomers, including cyclic isomers such as cyclohexane, methylcyclohexane and the like; as well as blends of alkanes with volatile aprotic solvents which do not initiate polymerization of cyanoacrylate monomers. Numerous aprotic solvents have utility including acetates such as methyl and ethyl acetate, propylene glycol diacetate, volatile ketones such as acetone and methyl ethyl ketone, volatile ethers such as diethyl ether, ethyl propyl ether, dipropyl ether and dipropylene glycol dimethyl ether, volatile fluorocarbons, such as pentafluoropropane, perfluoroheptane, perfluoromethylcyclohexane and the like; or a volatile gas, such as carbon dioxide, can also be employed, each with varying degrees of user discomfort. In one embodiment, the non-stinging, non-irritating, volatile non-reactive liquid is present from about 40% up to 99.9%, in another embodiment, 65% up to 99%, in another embodiment 75% to 90%, by weight of the total conformable coating composition.

Overall, in one embodiment, the total solids content of the conformable coating composition is at least 20% wt., and in one embodiment is at least 30% wt., and in one embodiment is less than 50% wt. of the total conformable coating composition.

The use of these non-stinging, non-irritating, volatile, non-reactive liquids, simply or in combination, as the primary liquid phase of the liquid coating, provide for rapid drying and less coating tackiness during drying is disclosed in U.S. Pat. No. 7,641,893, the disclosure of U.S. Pat. No. 7,641,893 is herein incorporated by reference. In one embodiment of the present disclosure, the volatile liquid portion evaporates so that the dried film forms in less than 2 minutes. In one embodiment, the dried film forms in less than 90 seconds. The use of these volatile non-reactive liquids inhibits adhesion of two surfaces to each other while allowing for good adhesion of the coating to its applied surface. During evaporation, the volatile non-reactive liquid solvent, having a low surface energy, is predominantly found on the air interface or "top" surface of the coating, hence inhibiting the cyanoacrylate from reaching the surface of the liquid coating and preventing an adherent bond to other surfaces that may be present. The relatively high volatile liquid content results in a composition does not create an adhesive bond which exceeds 45 grams shear force over a 6.5 $cm^2$ area after 10 min. contact time to a second glass surface, when: (i) the composition is applied to a first glass surface, and (ii) the second glass surface is applied to the first glass surface, having the composition disposed there between, wherein the composition forms an adherent, conformable polymer coating when applied to a surface.

In a published article titled, "The Extensibility in Human Skin: Variation According to Age and Site", British Journal of Plastic Surgery (1991), 44, 418-422, skin extensibility depended on the body site, age but in general ranged from 10% to over 60%. The desired range of elongation for the conformable coating should be at least 10%, preferably greater than 50% and most preferably greater than 100%.

Use of an elastomer in the conformable coating composition significantly increases the elongation capabilities of the coating. Therefore, the coating can stretch and recover while maintaining a continuous coating and limited cracks or breaks in the coating. In one embodiment the coating has an elongation of greater than 50%. In one embodiment, the coating has a percent fracture less than 75% when subject to 100% elongation. In one embodiment, the coating has a percent fracture is less than 75% when subject to 200% elongation. The disclosed coating is a significantly more durable and flexible barrier film when applied on such flexible surfaces such as skin.

Cyanoacrylate coating tend to be brittle and not flexible. Typically cured octyl cyanoactylate is more flexible than cured butyl cyanoactylate which is more flexible than cured ethyl cyanoacrylate. Further, relatively high elastomer content would tend to increase the tackiess of the surface of the coating. However, the disclosed systems were durable, flexible and relatively smooth. In particular, use of the relatively high elastomer, and rubber in particular, with butyl cyanoacrylate results in a durable and smooth, low coefficient of friction coating.

Other substances may be added to the liquid material or formulation for additional plasticization, tackifiers for improved adhesion, or rheology control, and the like, with the proviso that they do not induce spontaneous polymerization of the cyanoacrylate monomer.

It is believed that the coating formed from the conformable coating composition are multiphase and that the polycyanoacrylate is largely phase separated from the elastomeric phase. In considering plasticizers or tackifying adhesion promoters it is important to consider which polymer phase (elastomer or cyanoacrylate) they may not be compatible in. For this reason a broad range of plasticizers and tackifiers can be useful, including dibutylphthalate, acetyl tributyl citrate, sucrose acetate isobutyrate, sucrose benzoate, acetyltriethyl citrate, benzyl-(2-ethylhexyl) adipate, di-butyl adipate, hydrogenated polyisobutylene, mineral oil, decamethylcyclopentasiloxane, octamethylcyclotetrasiloxane, poly(methyphenylsiloxane), butyl glycolate and others. The plasticizing agent contains little or no moisture and should not significantly affect the polymerization of the cyanoacrylate monomer. Suitable plasticizers include polymeric plasticizers, such as poly(ethylene glycol) (PEG) esters and capped PEG esters or ethers, polyester glutarates and polyester adipates. Other compositions are exemplified by U.S. Pat. Nos. 5,259,835 and 5,328,687; 5,981,621; 6,143,352; 6,565,840; 6,010,714; 6,217,603; and 5,928,611, all incorporated by reference herein in their entirety.

Typical rheology additives that may be added to the liquid material or formulation are fumed silica, bentonite and other clay derivatives, and the like, provided that they do not cause polymerization of the cyanoacrylate monomer. Fillers can also be useful in modifying the slip, hardness and blocking performance of the coating. Large particles such as glass beads can be utilized to reduce the blocking performance of the coating.

The composition may optionally also include thickeners, although the elastomers typically impart significant thickening to the system and hence do not typically require additional thickening. Suitable thickeners include, for example, polycyanoacrylates, polycaprolactone, polyorthoesters, polyalkyl acrylates, copolymers of alkyl acrylate and vinyl acetate, poly(alkyl methacrylate)s, and copolymers of alkyl methacrylates and butadiene. Examples of alkyl methacrylates and acrylates are poly(methyl methacrylate), poly(2-ethylhexyl methacrylate) and poly(2-ethylhexyl acrylate), also poly(butyl methacrylate) and poly(butyl acrylate), also copolymers of various acrylate and methacrylate monomers, such as poly (butyl methacrylate-co-methyl acrylate).

The compositions may also include pH modifiers to control the rate of degradation of the resulting polymer, as disclosed in U.S. Pat. No. 6,143,352, the disclosure of which is herein incorporated by reference.

To improve the cohesive strength of adhesives formed from the compositions of this invention, difunctional monomeric crosslinking agents in concentration of less than 2 wt % of the composition may be added. Such crosslinking agents are known such as in U.S. Pat. No. 3,940,362.

The compositions may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, the disclosure of which is incorporated by reference herein in its entirety. Examples of suitable colorants as described in U.S. Pat. No. 5,981,621 include 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

The use of florescent dyes and pigments are also beneficial by enabling the coating to be viewed under black-light. The coating would be clear and transparent under normal lighting so the site can be easily viewed and inspected for changes in the skin. As a means of ensuring the coating is intact and covering the desired area, the site can be inspected by the use of a backlight wand or flashlight which reveals the coating by its florescence. A particularly useful hydrocarbon soluble fluorescing dye is 2,5-BIS(5-TERT-BUTYL-2-BENZOXAZOLYL) 1 THIOPHENE.

The compositions may also include one or more polymerization stabilizers for the cyanoacrylate monomer, preferably both at least one anionic vapor phase stabilizer and at least one anionic liquid phase stabilizer. Such stabilizing agents may also include mixtures of anionic stabilizing agents and radical stabilizing agents. These stabilizing agents may inhibit premature polymerization. Suitable stabilizers may include those listed in U.S. Pat. No. 6,183,593, the disclosure of which is incorporated by reference herein in its entirety.

Although specific embodiments have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

EXAMPLES

Objects and advantages of this invention are further illustrated by the following examples, but the particular materials and amounts thereof recited in these examples, as well as other conditions and details, should not be construed to unduly limit this invention.

Materials
Materials utilized for the examples are shown in Table 1.

TABLE 1

Materials List

| Compound | Source | Description |
| --- | --- | --- |
| Permethyl 104A | Presperse, Somerset, NJ | Polyisobutene (PIB), 900 MW |
| Permethyl 106A | Presperse, Somerset, NJ | Polyisobutene (PIB), 2,000 MW |
| Oppanol B15SFN | BASF Corp., Florham Park, NJ | Polyisobutene (PIB), 75,000 MW |
| Oppanol B30SF | BASF Corp., Florham Park, NJ | Polyisobutene (PIB), 200,000 MW |
| Oppanol B10 SFN | BASF Corp., Florham Park, NJ | Polyisobutene (PIB), 36,000 MW |
| Oppanol B80SF | BASF Corp., Florham Park, NJ | Polyisobutene (PIB), 750,000 MW |
| Isooctane | GFS Chemicals, Powell, OH | Isooctane (2,2,4 Trimethylpentane) |
| BCA | Cyberbond LLC, Batavia, IL | Butyl cyanoacrylate |
| OCA | Cyberbond LLC, Batavia, IL | Octyl cyanoacrylate |
| Giovarez 1800 | Phoenix Chemical Co., Somerville, NJ | Polyvinyl stearyl ether |
| Dimethicone L-45 1,000 | Crompton Corp., Greewich CT | Dimethicone, 1,000 cps |
| G1657 | Kraton ™ Polymers U.S. LLC, Houston, TX | Styrene, ethylene/butylenes triblock copolymer |
| TRIS (TRIS-MMA-IOA terpolymer) | 3M Company, St. Paul, MN | Poly(3-methacryloyloxypropyltris(trimethylsiloxy)silane (TRIS)-co-methyl methacrylate-co-isooctyl acrylate, 25% solids in isooctane |
| DMS-H21 | Gelest, Inc., Morrisville, PA | Hydride terminated polydimethylsiloxane, 4,000-5,000 MW |
| R-156 | Cray Valley, Exton, PA | Ricon-156, Polybutadiene, 1,400 MW |
| MD-6951 | Kraton Polymers, Houston, TX | Styrene, ethylene/butylenes triblock copolymer, 34% styrene content |
| SIP6830.3 | Gelest, Inc., Morrisville, PA | Platinum-divinyltetramethyldisiloxane complex |
| Crodamol ™ MM | Croda Inc., Edison NJ | Myristyl myristate |
| Polystyrene | Polysciences, Inc., Warrington, PA | Polystryene, 800-5000 MW |
| Sibstar 073T | Kaneka Corporation, Pasadena, TX | Thermoplastic Elastomer |
| G1730 | Kraton ™ Polymers U.S. LLC, Houston, TX | Styrene Ethylene Propylene Styrene Block Copolymer |
| G2836 | Kraton ™ Polymers U.S. LLC, Houston, TX | Styrene-Ethylene/Butylene-Styrene Copolymer |
| KIC11-819 | Kraton ™ Polymers U.S. LLC, Houston, TX | Styrene-Ethylene/Butylene-Styrene Copolymer |
| SL-167 | Zeon Chemicals L.P., Louisville, KY | SIS Block Copolymers |
| SL-169 | Zeon Chemicals L.P., Louisville, KY | SIS Block Copolymers |
| SL-159 | Zeon Chemicals L.P., Louisville, KY | SIS Block Copolymers |

Test Methods
Drag

Drag is a sensory evaluation conducted by lightly rubbing the cured coatings with a finger. The coatings were rated a 1 (low), 2 (slight), 3 (moderate), or 5 (high).

Tack

Tack is a sensory evaluation conducted by lightly touching the dried coatings on the gel with a finger. The coatings were rated from 1 (no tack) to 5 (tacky like a pressure sensitive adhesive).

Elongation

Several drops of each formulation were spread across a 2.54 cm×5.08 cm CHG gel pad (for example, 3M Tegaderm™ CHG Dressing, catalogue #1657, 3M Company, St. Paul, Minn.). The formulation was spread to a thin film and was allowed to dry (cure) for at least 15 minutes at room temperature. The CHG gel pads were then stretched to 100% or 200% of their initial length and placed on a flat surface so that they remained in their stretched position. Several drops of common bleach were placed on top of the coated gel. If the coating had fractured, the NaOCl in the bleach reacted with the CHG in the gel pad to form a brown color. After application of the bleach, the cured formulations were visually assessed and the amount of brown coloration was reported as a percent fracture. A reported value of F (fail) indicates >75% fracture. A reported value of P (pass) indicates no brown coloration.

Durability

A small amount of dry iron oxide red pigment was applied to skin. Two drops of each formulation was applied on top of the red pigment, spread into a 1 inch circle with a pipette tip, and allowed to dry (cure). The cured formulation was worn for 7 days. At day 7, a magnifying glass was used to visually assess the cured formulation. The percent of the 1 inch circle remaining was reported.

Examples

E-1

PIB (0.29 g) and isooctane (3.40 g), were combined in a sealed glass vial and heated to 60° C. until the polymer dissolved (24-48 hours). The solution was cooled to room temperature and the BCA (0.20 g) and OCA (0.11 g) added. The vial was then shaken until no solids remained.

E-2 through E-64

Examples were prepared as per E-1 with the formulations described in Tables 2 and 3.

E-65 through E-70

Examples were prepared as per E-1 with the Kraton™ G1657 and optional anti-blocking agent added with the PIB prior to heating. The compositions and test results are shown in Table 4.

E-71 through E-74

In a glass vile were mixed modifier (Crodomol™ MM), MD-6951, and cyclohexane. The vial was sealed and heated to 65° C. with mixing until all components were dissolved (24-48 hours). This solution was then cooled to room temperature and BCA was added. The vial was sealed and mixed until no solids remained and the solution appeared uniform. Compositions and test results are shown in Tables 5 and 6.

E-75 through E-83

In a three-neck, round-bottomed flask equipped with a reflux condenser, thermometer, and a nitrogen inlet was placed R-156 (28.0 g), DMS-H21 (12.0 g), and isooctane (160.0 g). The contents of the flask were stirred with a magnetic stir bar under nitrogen atmosphere at room temperature. Once all the components completely dissolved, SIP6830.3 (0.027 g) was added to the reaction and the flask was heated to 80° C. After 5 hours, the reaction was cooled to room temperature. This is the functionalized rubber.

The rubber components (functionalized and non-functionalized) and solvent (85/15 isooctane/ethylacetate) were combined in a sealed glass vial and heated to 60° C. until dissolved (24-48 hours). The solution was cooled to room temperature and the BCA was added. The vial was then shaken until no solids remained. E-76 through E-83 were prepared in a similar manner with the compositions shown in Tables 6 and 7.

Comparatives

C-1 through C-3

Comparatives were prepared by mixing the TRIS terpolymer with BCA. Formulations are provided in Table 8.

Results

Several polyisobutylene rubbers, with a variety of molecular weight, were formulated with BCA and OCA. Formulations and test results of the cured coatings are shown in Table 2. Durable, low drag formulations were obtained.

TABLE 2

Sample Formulations and Test Results

| | Formulation | | | | Test Results | |
|---|---|---|---|---|---|---|
| Sample | PIB [a] | (%) | BCA (%) | OCA (%) | Isooctane (%) | Drag | Durability (%) |
| E-1 | A | 7.3 | 5.0 | 2.8 | 85.0 | 2 | 1 |
| E-2 | A | 4.0 | 5.0 | 2.0 | 89.0 | 2 | 5 |
| E-3 | A | 4.0 | 5.0 | 4.0 | 87.0 | 2 | 2 |
| E-4 | A | 5.0 | 3.0 | 3.0 | 89.0 | 2 | 5 |
| E-5 | A | 8.0 | 3.0 | 4.0 | 85.0 | 2 | 1 |
| E-6 | A | 6.0 | 3.8 | 2.0 | 88.3 | 2 | 1 |
| E-7 | A | 9.0 | 3.0 | 2.0 | 86.0 | 2 | 1 |
| E-8 | A | 8.0 | 3.0 | 0.0 | 89.0 | 2 | 1 |
| E-9 | A | 4.0 | 7.0 | 0.0 | 89.0 | 2 | 10 |
| E-10 | A | 9.0 | 4.0 | 4.0 | 83.0 | 2 | 1 |
| E-11 | A | 6.0 | 7.0 | 4.0 | 83.0 | 2 | 0 |
| E-12 | B | 4.5 | 3.8 | 4.0 | 87.8 | 2 | 2 |
| E-13 | B | 4.8 | 4.8 | 3.0 | 87.5 | 2 | 5 |
| E-14 | B | 7.3 | 3.8 | 3.3 | 85.8 | 2 | 1 |
| E-15 | C | 5.3 | 5.0 | 2.0 | 87.8 | 3 | 20 |
| E-16 | C | 5.0 | 3.0 | 3.0 | 89.0 | 5 | 90 |
| E-17 | C | 9.0 | 3.8 | 2.0 | 85.3 | 5 | 90 |
| E-18 | D | 7.3 | 4.5 | 3.0 | 85.3 | 5 | 40 |
| E-19 | D | 6.0 | 4.0 | 4.0 | 86.0 | 5 | 40 |
| E-20 | D | 9.0 | 3.0 | 3.0 | 85.0 | 5 | 5 |
| E-21 | D | 4.0 | 3.0 | 4.0 | 89.0 | 5 | 40 |
| E-22 | D | 4.0 | 5.0 | 3.0 | 88.0 | 2 | 10 |
| E-23 | D | 6.0 | 3.0 | 2.0 | 89.0 | 3 | 40 |

TABLE 2-continued

Sample Formulations and Test Results

| | Formulation | | | Isooctane | Test Results | |
|---|---|---|---|---|---|---|
| Sample | PIB [a] | BCA (%) | OCA (%) | (%) | Drag | Durability (%) |
| E-24 | D | 4.8 | 4.0 | 2.3 | 89.0 | 3 | 20 |
| E-25 | D | 8.0 | 5.0 | 2.0 | 85.0 | 3 | 85 |
| E-26 | D | 4.0 | 7.0 | 0.0 | 89.0 | 2 | 99 |
| E-27 | D | 9.0 | 7.0 | 1.0 | 83.0 | Not tested | 80 |
| E-28 | D | 4.0 | 7.0 | 4.0 | 85.0 | Not tested | 20 |
| E-29 | D | 7.3 | 3.0 | 2.8 | 87.0 | 2 | 85 |
| E-30 | D | 9.0 | 3.0 | 0.0 | 88.0 | 5 | 99 |
| E-31 | D | 6.0 | 5.0 | 0.0 | 89.0 | 5 | 95 |
| E-32 | D | 7.0 | 7.0 | 3.0 | 83.0 | 3 | 40 |
| E-33 | E | 7.3 | 4.5 | 3.0 | 85.3 | 5 | 40 |
| E-34 | E | 6.0 | 4.0 | 4.0 | 86.0 | 5 | 40 |
| E-35 | E | 9.0 | 3.0 | 3.0 | 85.0 | 5 | 5 |
| E-36 | E | 4.0 | 3.0 | 4.0 | 89.0 | 5 | 40 |
| E-37 | E | 4.0 | 5.0 | 3.0 | 88.0 | 2 | 10 |
| E-38 | E | 6.0 | 3.0 | 2.0 | 89.0 | 3 | 40 |
| E-39 | F | 7.8 | 3.5 | 3.8 | 85.0 | 5 | 95 |
| E-40 | F | 6.0 | 5.0 | 4.0 | 85.0 | 5 | 85 |

[a] A = Permethyl 104A B = Permethyl 106A C = Oppanol B15SFN D = Oppanol B80SF E = Oppanol B10SFN F = Oppanol B30SF Formulations containing optional Kraton™ G1657 rubber and test results of the cured coatings are shown in Table 3. Durable, flexible coatings were obtained.

TABLE 3

Formulations Containing Kraton ™ Rubber

| | Formulation | | | | | Test Results | | |
|---|---|---|---|---|---|---|---|---|
| | | | | | | Fracture (%) | | |
| Sample | PIB (%) [a] | BCA (%) | G1657 (%) | OCA (%) | Isooctane (%) | 100% Elongation | 200% Elongation | Durability [b] (%) |
| E-41 | A | 4.0 | 3.0 | 6.0 | 2.0 | 85.0 | P | 10 | 100 |
| E-42 | A | 4.0 | 3.8 | 4.1 | 3.2 | 85.0 | P | 10 | 5 |
| E-43 | A | 4.0 | 3.0 | 1.0 | 4.0 | 88.0 | 50 | F | 0 |
| E-44 | A | 4.0 | 5.0 | 1.0 | 2.0 | 88.0 | F | F | 5 |
| E-45 | A | 3.0 | 5.0 | 3.0 | 4.0 | 85.0 | 50 | F | 4 |
| E-46 | A | 2.9 | 3.0 | 3.1 | 2.0 | 89.0 | P | F | 1 |
| E-47 | A | 1.5 | 4.8 | 3.3 | 2.7 | 87.7 | 75 | F | 20 |
| E-48 | A | 1.5 | 3.3 | 2.6 | 3.6 | 89.0 | F | F | 60 |
| E-49 | A | 0.7 | 3.5 | 5.5 | 2.2 | 88.1 | P | 25 | 30 |
| E-50 | A | 0.0 | 5.0 | 2.0 | 4.0 | 89.0 | F | F | 0 |
| E-51 | A | 0.0 | 5.0 | 6.0 | 2.0 | 87.0 | P | P | 100 |
| E-52 | A | 0.0 | 3.0 | 6.0 | 4.0 | 87.0 | 10 | 25 | 20 |
| E-53 | C | 3.2 | 4.2 | 1.7 | 2.6 | 88.4 | F | F | 15 |
| E-54 | C | 2.4 | 3.2 | 6.0 | 3.1 | 85.4 | P | P | 50 |
| E-55 | C | 0.0 | 4.1 | 3.8 | 3.3 | 88.9 | 50 | 75 | 1 |
| E-56 | D | 4.0 | 3.0 | 4.0 | 4.0 | 85.0 | P | P | 20 |
| E-57 | D | 4.0 | 5.0 | 4.0 | 2.0 | 85.0 | P | P | 80 |
| E-58 | D | 4.0 | 3.0 | 2.0 | 2.0 | 89.0 | P | P | 90 |
| E-59 | D | 4.0 | 5.0 | 1.0 | 4.0 | 86.0 | P | P | 30 |
| E-60 | D | 2.8 | 4.4 | 4.1 | 3.7 | 85.0 | P | P | 10 |
| E-61 | D | 1.4 | 5.0 | 2.6 | 2.0 | 89.0 | 10 | 25 | 50 |
| E-62 | D | 1.3 | 3.0 | 2.7 | 4.0 | 89.0 | P | P | 20 |
| E-63 | D | 0.0 | 5.0 | 6.0 | 4.0 | 85.0 | 25 | 25 | 2 |
| E-64 | D | 0.0 | 3.0 | 6.0 | 2.0 | 89.0 | P | P | 50 |

[a] A = Permethyl 104A C = Oppanol B15SFN D = Oppanol B80SF
[b] Durability measured at day 8

Formulations containing additional anti-blocking agents and test results of the cured coatings are shown in Table 4. Isooctane was used as the diluent. The formulations containing the anti-blocking agents were clear and produced clear cured films.

TABLE 4

Formulations Containing Anti-Blocking Agents

| Sample | PIB [a] (%) | BCA (%) | Anti-Blocking Agent (%) | G1657 (%) | % Isooctane | Fracture (%) 100% Elongation | Fracture (%) 200% Elongation | Durability (%) |
|---|---|---|---|---|---|---|---|---|
| E-65 | 4.2 | 6.0 | 0 | 1.8 | 88.0 | F | F | 50 |
| E-66 | 5.5 | 4.2 | 0 | 2.3 | 88.0 | 10 | 30 | 50 |
| E-67 | 2.7 | 4.2 | 0 | 5.1 | 88.0 | 10 | F | 40 |
| E-68 | 5.5 | 4.2 | 3.0[b] | 2.3 | 85 | 2 | 40 | 100 |
| E-69 | 5.5 | 4.2 | 3.0[c] | 2.3 | 85 | 20 | 20 | 100 |
| E-70 | 5.5 | 4.2 | 3.0[d] | 2.3 | 85 | 20 | 40 | 40 |

[a] Oppanol 50
[b] Cetyl palmitate
[c] Polyvinyl stearyl ether
[d] Dimethicone

Formulations containing the elastomer-phase modifiers Crodamol™ MM and polystyrene are shown in Table 5.

TABLE 5

Formulations Containing Elastomer Phase Modifiers

| Sample | Modifier (%) | BCA (%) | MD-6951 (%) | Cyclohexane (%) | Fracture (%) 100% Elongation | Fracture (%) 200% Elongation | Durability [a] (%) |
|---|---|---|---|---|---|---|---|
| E-71 | 2.0[b] | 7.0 | 12.5 | 78.5 | P | 3 | 70 |
| E-72 | 2.0[c] | 7.0 | 12.5 | 78.5 | P | 10 | 60 |
| E-73 | 5.0[c] | 7.0 | 12.5 | 75.5 | 20 | P | 50 |
| E-74 | 10.0[c] | 7.0 | 12.5 | 70.5 | 2 | 1 | 40 |

[a] Durability measured at 3 days
[b] Crodamol™ MM
[c] Polystyrene

Formulations with siliconized rubber are shown in Tables 6 and 7.

TABLE 6

Formulations Containing Siliconized Rubber

| Sample | Siliconized Rubber (%) | R-156 (%) | MD-6951 (%) | BCA (%) | Ethyl Acetate (%) | Iso-Octane (%) | Fracture at 200% Elongation | Tack | Drag |
|---|---|---|---|---|---|---|---|---|---|
| E-75 | 2.5 | 0 | 15 | 6.8 | 12.6 | 63.1 | P | 1 | 1 |
| E-76 | 0.8 | 3.3 | 15 | 6.8 | 13.3 | 60.9 | P | 2 | 2 |

TABLE 7

Formulations Containing Siliconized Rubber

| Sample | Siliconized Rubber (%) | Rubber (%) | BCA (%) | Cyclohexane (%) | Fracture (%) 100% Elongation | Fracture (%) 200% Elongation | Drag |
|---|---|---|---|---|---|---|---|
| E-77 | 3.0 | Sibstar™ 12.5 | 7.0 | 76.5 | 1 | 4 | 1 |
| E-78 | 3.0 | G1730 12.5 | 7.0 | 76.5 | P | 1 | 2 |
| E-79 | 3.0 | G2836 12.5 | 7.0 | 76.5 | 5 | P | 2 |
| E-80 | 3.0 | KIC11- 12.5 | 7.0 | 76.5 | P | 7 | 2 |

TABLE 7-continued

Formulations Containing Siliconized Rubber

| | Formulation | | | | Test Results | | |
|---|---|---|---|---|---|---|---|
| | Siliconized | | | | Fracture (%) | | |
| Sample | Rubber (%) | Rubber (%) | BCA (%) | Cyclohexane (%) | 100% Elongation | 200% Elongation | Drag |
| E-81 | 3.0 | SL-167 | 12.5 | 7.0 | 76.5 | P | 1 | 2 |
| E-82 | 3.0 | SL-169 | 12.5 | 7.0 | 76.5 | 20 | 1 | 2 |
| E-83 | 3.0 | SL-159 | 12.5 | 7.0 | 76.5 | 20 | 24 | 1 |

Comparative formulations containing TRIS and BCA, diluted with HDMS were prepared and tested as shown in Table 8. These cured formulations were not flexible or durable.

TABLE 8

TRIS Formulations

| | | Formulation | | | Test Results | | |
|---|---|---|---|---|---|---|---|
| | TRIS | | | | Fracture (%) | | |
| Sample | Terpolymer (%) | BCA (%) | Isooctane (%) | HMDS (%) | 100% Elongation | 200% Elongation | Durability (%) |
| C-1 | 8 | 4 | 24 | 64 | F | F | 30 |
| C-2 | 6 | 6 | 18 | 70 | F | F | 5 |
| C-3 | 4 | 8 | 12 | 76 | F | F | 5 |

What is claimed is:

1. A conformable coating composition comprising:
   a polymerizable cyanoacrylate monomer;
   an elastomer;
   a volatile liquid;
   wherein the cyanoacrylate monomer is 0.1 to 65% wt. of the nonvolatile portion;
   wherein the elastomer in an elastomer phase is at least 35% wt. of the nonvolatile portion;
   wherein the volatile liquid is at least 40% wt. of the total composition; and
   wherein the composition does not create an adhesive bond which exceeds 45 grams shear force over a 6.5 cm$^2$ area after 10 min. contact time to a second glass surface, when: (i) the composition is applied to a first glass surface, and (ii) the second glass surface is applied to the first glass surface, having the composition disposed there between, wherein the composition forms an adherent, conformable polymer coating when applied to a surface.

2. The composition of claim 1, wherein said polymerizable cyanoacrylate monomer component comprises alpha-cyanoacrylates.

3. The composition of claim 1, comprising 0.1 to 55% wt. of the nonvolatile portion of the polymerizable cyanoacrylate monomer.

4. The composition of claim 1, wherein the volatile liquid is selected from the group consisting of volatile linear and cyclic siloxanes, volatile polydimethylsiloxanes; C6 to C10 alkanes and their structural isomers; volatile aprotic solvents; volatile ketones; volatile ethers, and combinations thereof.

5. The composition of claim 1, wherein the volatile liquid is selected from the group consisting of heptane, isooctane, octane, nonane, and decane, cyclohexane, methylcyclohexane, methyl acetate, ethyl acetate, propylene glycol diacetate, acetone, methyl ethyl ketone, diethyl ether, ethyl propyl ether, dipropyl ether, dipropylene glycol dimethyl ether, and combinations thereof.

6. The composition of claim 1, comprising at least 60% wt. of the total composition of the volatile liquid.

7. The composition of claim 1, wherein the elastomer is a rubber or a thermoplastic elastomer.

8. The composition of claim 7, wherein the rubber is selected from the group consisting polyisobutylenes, polyisoprenes, butyl rubber, halogenated butyl rubbers, dienes, styrene copolymers, acrylonitrile copolymers, and copolymers or mixtures thereof, which are soluble or highly swollen in the volatile liquid.

9. The composition of claim 1, wherein the elastomer is chemically modified with a low surface energy material.

10. The composition of claim 9, wherein the low surface energy material is silicone, fluorinated oligomers, or hydrocarbon based oligomeric material.

11. The composition of claim 1, wherein the viscosity is less than 1,000 cps.

12. The composition of claim 1, wherein the volatile liquid evaporates from a surface to form a conformable film in less than 2 minutes.

13. The composition of claim 12, wherein the film fractures less than 75% at 100% elongation.

14. The composition of claim 9, wherein the elastomer is an unsaturated rubber.

* * * * *